United States Patent
Klima et al.

(10) Patent No.: US 10,660,752 B2
(45) Date of Patent: May 26, 2020

(54) RETAINERS FOR TRANSCATHETER HEART VALVE DELIVERY SYSTEMS

(71) Applicant: St. Jude Medical, Cardiology Division, Inc., St. Paul, MN (US)

(72) Inventors: Daniel J. Klima, Andover, MN (US); Michael Shane Morrissey, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 212 days.

(21) Appl. No.: 15/921,759

(22) Filed: Mar. 15, 2018

(65) Prior Publication Data

US 2018/0263772 A1   Sep. 20, 2018

Related U.S. Application Data

(60) Provisional application No. 62/472,074, filed on Mar. 16, 2017.

(51) Int. Cl.
*A61F 2/24* (2006.01)
*A61F 2/966* (2013.01)
*A61F 2/95* (2013.01)

(52) U.S. Cl.
CPC .......... *A61F 2/2436* (2013.01); *A61F 2/2412* (2013.01); *A61F 2/2418* (2013.01);
(Continued)

(58) Field of Classification Search
CPC ................ A61F 2/2412; A61F 2/2418; A61F 2002/9517; A61F 2002/9665; A61F 2/24;
(Continued)

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| DE | 102005003632 A1 | 8/2006 |
| EP | 1129744 A1 | 9/2001 |

(Continued)

OTHER PUBLICATIONS

International Search Report including Written Opinion for PCT/US2018/022542 dated May 29, 2018.
(Continued)

*Primary Examiner* — George J Ulsh
(74) *Attorney, Agent, or Firm* — Lerner, David, Littenberg, Krumholz & Mentlik, LLP

(57) ABSTRACT

A delivery device for an implantable medical device includes an inner shaft extending in a longitudinal direction and an outer sheath adapted to surround at least a portion of the inner shaft, the outer sheath being slideable relative to the inner shaft in the longitudinal direction. A compartment defined between the inner shaft and the outer sheath is adapted to receive the medical device in an assembled condition. A retaining assembly positioned at one end of the compartment includes a first member rotatable with respect to the inner shaft, and a second member rotationally fixed with respect to the inner shaft. The medical device includes at least one retainer adapted to be received within at least one retainer slot of the first member. This arrangement enables the medical device to rotate within the compartment as the delivery device is advanced to an implantation site.

20 Claims, 10 Drawing Sheets

(52) U.S. Cl.
CPC ...... *A61F 2/966* (2013.01); *A61F 2002/9517* (2013.01); *A61F 2002/9665* (2013.01)

(58) Field of Classification Search
CPC .. A61F 2/2427; A61F 2/95; A61F 2002/9505; A61F 2/2436; A61F 2/2439; A61F 2/962; A61F 2002/9522; A61F 2/966; A61F 2/00; A61F 2/0022; A61F 2/04; A61F 2/07; A61F 2002/0852; Y10T 29/49925
USPC ...................................................... 623/2.11
See application file for complete search history.

(56) References Cited

U.S. PATENT DOCUMENTS

| | | | |
|---|---|---|---|
| 5,078,720 | A | 1/1992 | Burton et al. |
| 5,415,664 | A | 5/1995 | Pinchuk |
| 5,484,444 | A | 1/1996 | Braunschweiler et al. |
| 5,702,418 | A | 12/1997 | Ravenscroft |
| 5,824,041 | A | 10/1998 | Lenker et al. |
| 5,843,167 | A | 12/1998 | Dwyer et al. |
| 5,924,424 | A | 7/1999 | Stevens et al. |
| 5,968,068 | A | 10/1999 | Dehdashtian et al. |
| 5,980,533 | A | 11/1999 | Holman |
| 6,077,297 | A | 6/2000 | Robinson et al. |
| 6,269,819 | B1 | 8/2001 | Oz et al. |
| 6,306,141 | B1 | 10/2001 | Jervis |
| 6,391,050 | B1 | 5/2002 | Broome |
| 6,468,299 | B2 | 10/2002 | Stack et al. |
| 6,623,518 | B2 | 9/2003 | Thompson et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,311,730 | B2 | 12/2007 | Gabbay |
| 7,510,572 | B2 | 3/2009 | Gabbay |
| 7,682,390 | B2 | 3/2010 | Seguin |
| 7,803,185 | B2 | 9/2010 | Gabbay |
| 8,840,663 | B2 | 9/2014 | Salahieh et al. |
| 9,119,717 | B2 | 9/2015 | Wang et al. |
| 2003/0050694 | A1 | 3/2003 | Yang et al. |
| 2004/0210304 | A1 | 10/2004 | Seguin et al. |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0071369 | A1 | 3/2008 | Tuval et al. |
| 2008/0147182 | A1 | 6/2008 | Righini et al. |
| 2009/0054975 | A1 | 2/2009 | del Nido et al. |
| 2010/0004740 | A1 | 1/2010 | Seguin et al. |
| 2010/0286768 | A1 | 11/2010 | Alkhatib |
| 2010/0298931 | A1 | 11/2010 | Quadri et al. |
| 2011/0224678 | A1 | 9/2011 | Gabbay |
| 2011/0251675 | A1* | 10/2011 | Dwork ................. A61F 2/2418 623/1.23 |
| 2011/0264203 | A1* | 10/2011 | Dwork ................. A61F 2/2418 623/2.11 |
| 2015/0088245 | A1* | 3/2015 | Costello ................. A61F 2/95 623/2.11 |

FOREIGN PATENT DOCUMENTS

| | | |
|---|---|---|
| EP | 1157673 A2 | 11/2001 |
| EP | 1926455 A2 | 6/2008 |
| WO | 02067782 A2 | 9/2002 |
| WO | 2007053243 A2 | 5/2007 |
| WO | 07071436 A2 | 6/2007 |
| WO | 08070797 A2 | 6/2008 |
| WO | 2009053497 A1 | 4/2009 |
| WO | 2010051025 A1 | 5/2010 |
| WO | 2010087975 A1 | 8/2010 |
| WO | 2012009006 A1 | 1/2012 |
| WO | 2015063118 A1 | 5/2015 |

OTHER PUBLICATIONS

Quaden, Rene et al., Percutaneous aortic valve replacement: resection before implantation, 836-840, European J. of Cardio-thoracic Surgery, 27 (2005), pp. 5.

Ruiz, Carlos, Overview of PRE-CE Mark Transcatheter Aortic Valve Technologies, Euro PCR, dated May 25, 2010, pp. 14.

* cited by examiner

RETAINERS FOR TRANSCATHETER HEART VALVE DELIVERY SYSTEMS

CROSS-REFERENCE TO RELATED APPLICATIONS

This application claims the benefit of the filing date of U.S. Provisional Patent Application No. 62/472,074, filed Mar. 16, 2017, the disclosure of which is hereby incorporated by reference herein.

BACKGROUND OF THE DISCLOSURE

The present disclosure is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are at least two types of stents on which collapsible valves are mounted: self-expanding stents and balloon-expandable stents. To place a collapsible valve into a delivery apparatus and ultimately into a patient, the valve is first collapsed or crimped to reduce its circumferential size. When a collapsed valve has reached the desired implant site in the patient (e.g., at or near the annulus of the patient's heart valve that is to be replaced by the prosthetic valve), the prosthetic valve can be released from the delivery apparatus and re-expanded to full operating size.

Despite the various improvements that have been made to the collapsible prosthetic heart valve delivery process, conventional delivery devices, systems, and methods suffer from some shortcomings. For example, the self-expanding collapsible valve may include retainers that are inserted into corresponding retainer slots in a catheter to hold the valve in a desired position and/or orientation. During deployment of the self-expanding valve into the desired area (e.g., the aortic valve annulus), forces applied on the stent may restrict the ability of the stent retainers to fully release from the corresponding retainer slots of the catheter. There therefore is a need for further improvements to the devices, systems, and methods for transcatheter delivery of collapsible prosthetic heart valves.

BRIEF SUMMARY

According to one aspect of the disclosure, a delivery device for an implantable medical device having at least one retainer thereon includes an inner shaft extending in a longitudinal direction. An outer sheath is adapted to surround at least a portion of the inner shaft, the outer sheath being slideable relative to the inner shaft in the longitudinal direction. A compartment is defined between the inner shaft and the outer sheath and is adapted to receive the medical device in an assembled condition. A retaining assembly is positioned at one end of the compartment, the retaining assembly including a first member rotatable with respect to the inner shaft, and a second member rotationally fixed with respect to the inner shaft. At least one retainer slot in the first member is adapted to receive the retainer of the medical device in the assembled condition. Engagement between the first member and the second member limits rotation of the first member.

According to another aspect of the disclosure, a method of delivering a collapsible prosthetic valve to a patient includes providing the collapsible prosthetic valve which has a collapsible valve assembly mounted within a collapsible stent, the stent having a plurality of retainers extending therefrom. A delivery device is also provided, the delivery device including an inner shaft extending in a longitudinal direction, and an outer sheath adapted to surround at least a portion of the inner shaft. The delivery device includes a compartment defined between the inner shaft and the outer sheath, and a retaining assembly positioned at one end of the compartment. The retaining assembly includes a first member rotatable with respect to the inner shaft and a second member rotationally fixed with respect to the inner shaft. The method further includes loading the collapsible prosthetic valve into the compartment in a collapsed condition so that the retainers are received within corresponding retainer slots of the first member. The compartment is advanced to a site of implantation in the patient. The first member is rotated relative to the second member during the advancing step, wherein engagement between the first member and the second member limits rotation of the first member. The compartment is exposed by sliding the outer sheath relative to the inner shaft so that the collapsible prosthetic valve at least partially expands.

DETAILED DESCRIPTION

As used herein, the terms "proximal" and "distal," when used in reference to a delivery device, are to be taken as relative to a user of the delivery device. "Proximal" is to be understood as relatively close to the user and "distal" is to be understood as relatively far away from the user. As used herein, the terms "inflow" and "outflow," when used in reference to a prosthetic heart valve, are to be taken as relative to the intended direction of blood flow through the device. "Inflow" refers to the end of the valve into which blood flows, and "outflow" refers to the end of the valve out of which blood flows.

Figure 1:
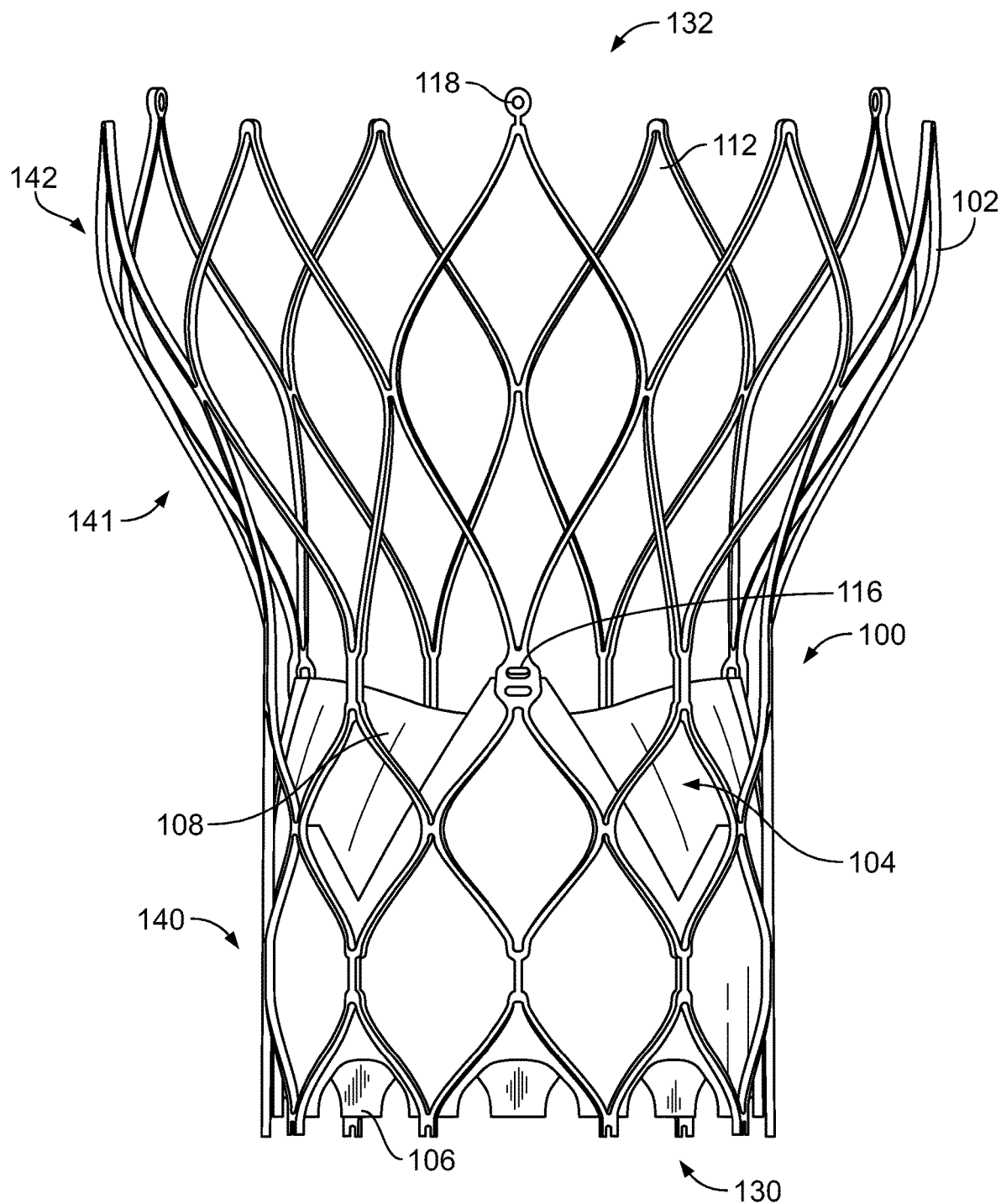
FIG. 1 is a front view of a collapsible prosthetic heart valve according to the prior art.

FIG. 1 shows a known collapsible stent-supported prosthetic heart valve 100 according to the prior art. The prosthetic heart valve 100 is designed to replace the function of a native aortic valve of a patient. The prosthetic heart valve 100 includes a stent constructed as a frame 102, which may be wholly or partly formed of any biocompatible material, such as metals, synthetic polymers, or biopolymers capable of functioning as a stent.

The stent 102 extends from an inflow or annulus end 130 to an outflow or aortic end 132, and includes an annulus section 104 adjacent the inflow end 130 and an aortic section 142 adjacent the outflow end 132. The annulus section 104 has a relatively small cross-section in the expanded condition, while the aortic section 142 has a relatively large cross-section in the expanded condition. The annulus section 104 may be in the form of a cylinder having a substantially constant diameter along its length. A transition section 141 may taper outwardly from the annulus section 104 to the aortic section 142. Each of the sections of the stent 102 includes a plurality of cells 112 connected to one another in one or more annular rows around the stent 102. For example, as shown in FIG. 1, the annulus section 104 may have two annular rows of complete cells 112 and the aortic section 142 and the transition section 141 may each have one or more annular rows of complete or partial cells 112. The cells 112 in the aortic section 142 may be larger than the cells 112 in the annulus section 104. The larger cells 112 in the aortic section 142 better enable the prosthetic valve 100 to be positioned without the stent structure 102 interfering with blood flow to the coronary arteries.

The stent 102 may include one or more retainers 118 at the outflow end 132 thereof, the retainers 118 being sized and shaped to cooperate with retainer slots provided on a deployment device described in greater detail below. The engagement of the retainers 118 with the retainer slots on the deployment device helps maintain the prosthetic heart valve 100 in an assembled relationship with the deployment device and minimizes longitudinal movement of the prosthetic heart valve relative to the deployment device during unsheathing or resheathing procedures. Although retainers 118 are illustrated as substantially circular members, it should be understood that the retainers may have other shapes. In addition, although retainers 118 are illustrated as extending from the outflow end 132 of the stent 102, some prosthetic valves may include retainers at an inflow end of the stent, depending on the particular valve and the desired route of delivery.

The prosthetic heart valve 100 includes a valve assembly 140 positioned in the annulus section 104. The valve assembly 140 may include a cuff 106 and a plurality of leaflets 108 which collectively function as a one-way valve by coapting with one another. The valve assembly 140 may be mounted to the stent 102 by suturing the commissures where two leaflets 108 come together to commissure attachment features ("CAFs") 116 and suturing other portions of the valve assembly to the stent, or by other methods known in the art. The valve assembly 140 may be wholly or partly formed of any suitable biological material or polymer. Examples of biological materials suitable for the valve assembly 140 include, but are not limited to, porcine or bovine pericardial tissue. Examples of polymers suitable for the valve assembly 140 include, but are not limited to, polyurethane, silicone, PTFE and polyester. In at least some examples, portions of valve assembly 140, including leaflets 108, cuff 106 and the suture used may include an ultra-high molecular weight polyethylene.

FIG. 1 illustrates a prosthetic heart valve for replacing a native tricuspid valve, such as the aortic valve. Accordingly, the prosthetic heart valve 100 is shown in FIG. 1 with three leaflets 108, as well as three CAFs 116. The CAFs 116 may lie at the intersection of four cells 112, two of the cells 112 being adjacent one another in the same annular row, and the other two cells 112 being in different annular rows and lying in end-to-end relationship. In one embodiment, the CAFs 116 are positioned entirely within the annulus section 104 or at the juncture of annulus section 104 and the transition section 141. The CAFs 116 may include one or more eyelets which facilitate the suturing of the leaflet commissure to the stent. Although three leaflets 108 and three CAFs 116 are shown in FIG. 1, it should be appreciated that prosthetic heart valves suitable for use with the delivery devices disclosed herein may have a greater or lesser number of leaflets 108 and CAFs 116.

In operation, the embodiments of the prosthetic heart valve 100 described above may be used to replace a native heart valve, such as the aortic valve, a surgical heart valve or a heart valve that has undergone a surgical procedure. The prosthetic heart valve 100 may be delivered to the desired site (e.g., near a native aortic annulus) using a suitable delivery device, such as those disclosed below. During delivery, the prosthetic heart valve 100 is disposed inside the delivery device in the collapsed condition. The delivery device may be introduced into a patient using any known procedures, such as a transfemoral, transapical or transseptal approach. Once the delivery device has reached the target site, the user may deploy the prosthetic heart valve 100. Upon deployment, the prosthetic heart valve 100 expands into secure engagement within the native aortic annulus. When the prosthetic heart valve 100 is properly positioned inside the heart, it works as a one-way valve, allowing blood to flow in one direction and preventing blood from flowing in the opposite direction.

Figures 2, 3:
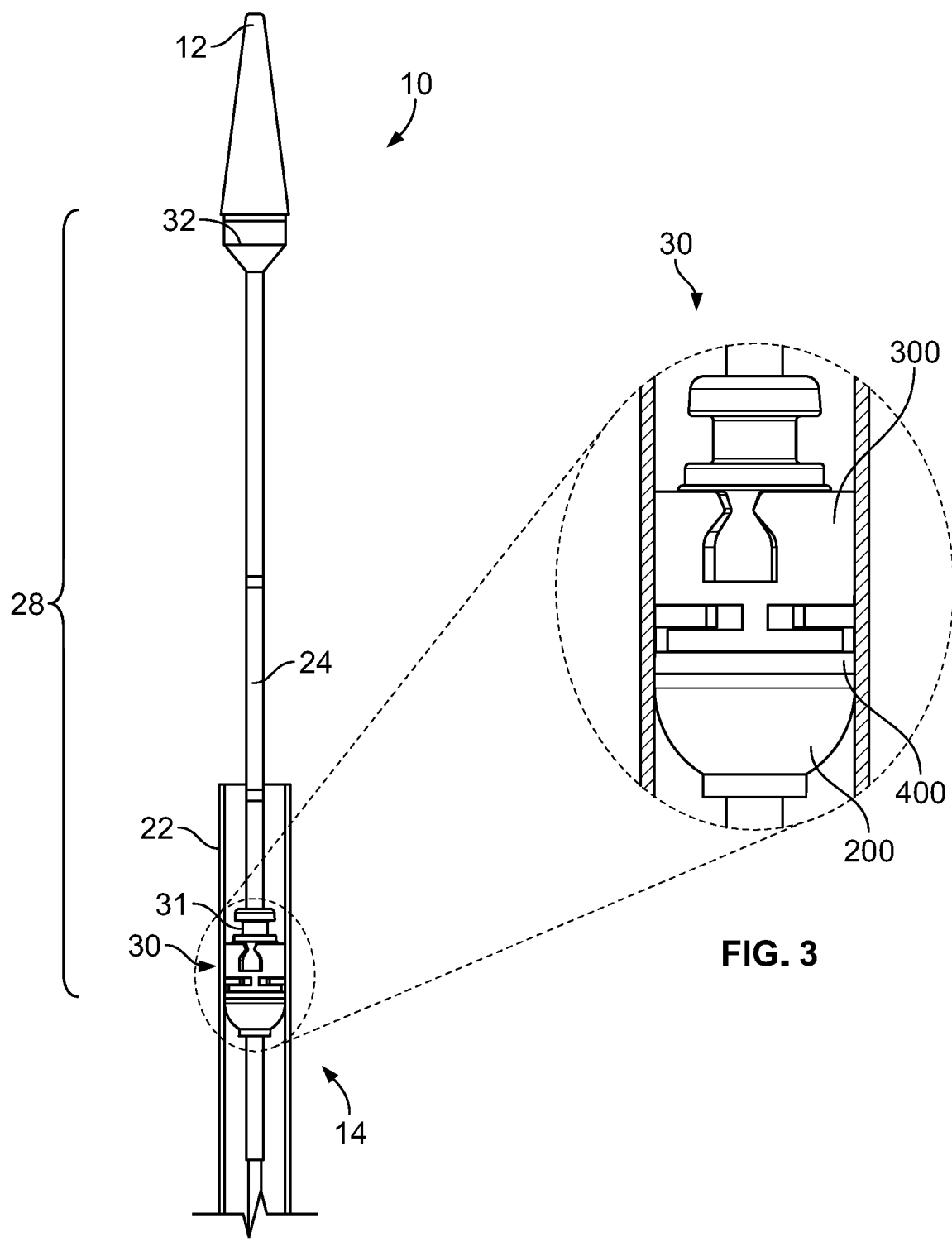
FIG. 2 is a side view of a distal portion of a transfemoral delivery device for a collapsible prosthetic heart valve.
FIG. 3 is an enlarged view of a retaining assembly of the delivery device of FIG. 2.

FIG. 2 illustrates the distal end of a delivery device 10 according to the present disclosure. Delivery device 10 may include a distal tip 12 and a catheter assembly 14 extending from the distal tip 12 to a proximal end that includes a handle (not shown) for a user to control the delivery device. The illustrated delivery device 10 may be particularly suited for transfemoral delivery of a collapsible prosthetic heart valve, although as is described in greater detail below, the concepts described in connection with delivery device 10 may be applied to delivery devices used to deliver a prosthetic heart valve using other approaches.

Catheter assembly 14 may include an outer sheath 22 extending from the handle towards the distal tip 12, a hollow inner shaft 24 slideable within the outer sheath 22 and extending from the handle to the distal tip 12, and a valve receiving compartment 28 configured to receive a collapsible prosthetic valve, such as prosthetic heart valve 100, in a collapsed condition for delivery inside of a patient.

The valve receiving compartment 28 includes a retaining assembly 30 located inside the outer sheath 22, a proximal conical end 31 adjacent the retaining assembly 30, and a distal conical end 32 spaced from the retaining assembly 30. It should be understood that although described as conical ends, ends 31 and 32 may have shapes other than conical. Conical end 32 may be joined to the inner shaft 24 at a distal end of the valve receiving compartment 28, and conical end 31 and the retaining assembly 30 may be joined to the inner shaft 24 at the proximal end of the valve receiving compartment 28. The inner shaft 24 may be adapted to receive a guide wire (not shown) therethrough so that the delivery device may be advanced over the guide wire which may have been previously advanced to the site of implantation. For delivery into a patient, a collapsible valve is loaded into the valve receiving compartment 28 around the inner shaft 24, with the inflow end 130 supported by conical end 32, the outflow end 132 supported by conical end 31 and the retainers 118 coupled to retainer slots in retaining assembly 30.

Retaining assembly 30 is shown in greater detail in FIG. 3. Retaining assembly 30 may include at least three components: a base member 200, a first retaining member 300, and a second retaining member 400.

Figure 4A:
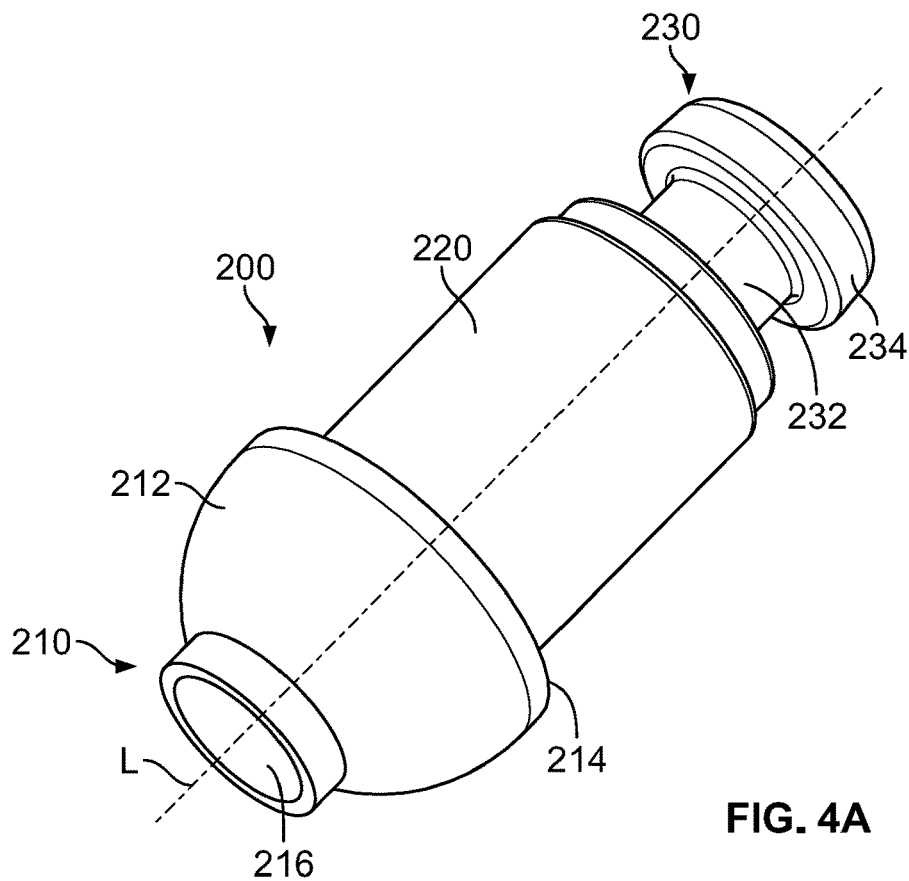
FIGS. 4A-B are perspective views of a base member of the retaining assembly of FIG. 3.
Figure 4B:
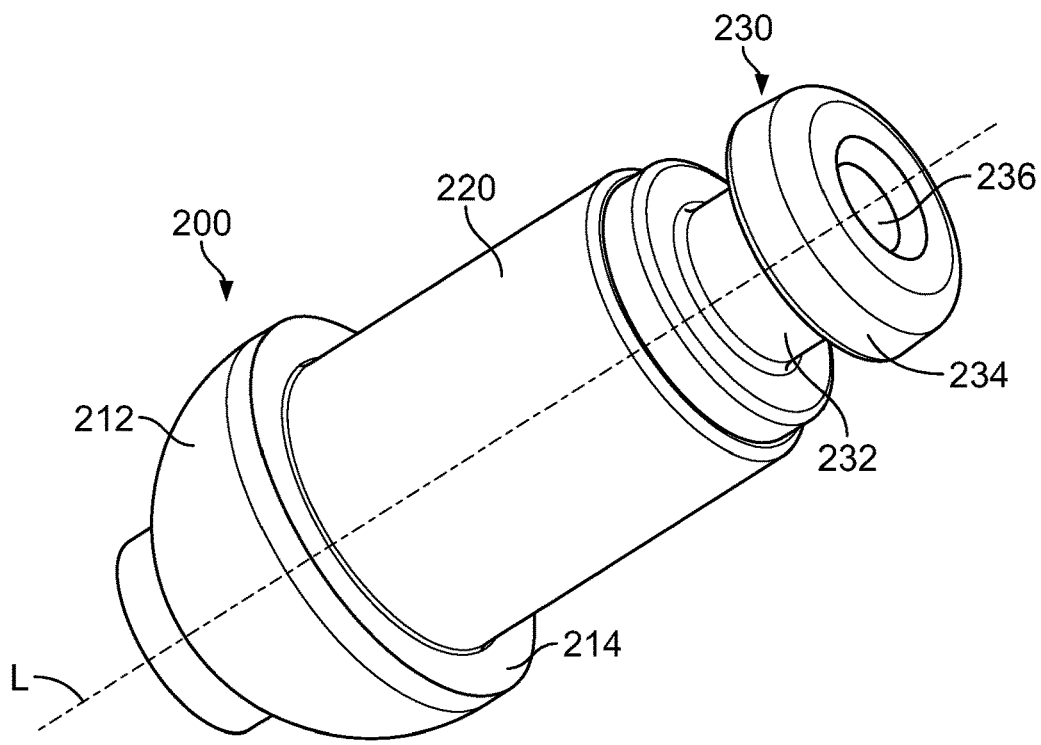

Base member 200 is shown isolated from other components of retaining assembly 30 in FIGS. 4A-B. Base member 200 extends from a proximal end 210 to a distal end 230 via a substantially cylindrical intermediate portion 220. The proximal end 210 may include a substantially hemispherical support member 212 having a diameter larger than the diameter of intermediate portion 220 so as to form a shoulder 214 at the juncture therebetween. A substantially circular longitudinal bore 216 may extend inward from proximal end 210 and may be shaped and dimensioned to receive inner shaft 24. As explained in greater detail below, intermediate portion 220 may serve as a support for the first retaining member 300 and the second retaining member 400. The distal end 230 of base member 200 includes a shaft 232 extending from intermediate portion 220 to a flange 234. Shaft 232 may be substantially cylindrical with a diameter smaller than that of intermediate portion 220, while flange 234 may also be substantially cylindrical, with a diameter larger than that of shaft 232. Flange 234 includes a longitudinal bore 236, which may be substantially circular and may be shaped and dimensioned to receive inner shaft 24. Longitudinal bore 236 may connect to longitudinal bore 216 so as to form a continuous bore extending through the length of base member 200. Conical end 31 may be snapped over, or otherwise connected to, the shaft 232 of distal end 230, with flange 234 acting to limit translation of the conical end with respect to base member 200. It should be understood that conical end 31 may be formed as part of retaining assembly 30, but the above-described configuration may facilitate assembly of the retaining assembly 30.

Base member 200 is assembled to inner shaft 24 so that the shaft is coincident with the longitudinal axis L of the base member. Preferably, base member 200 is both translationally and rotationally fixed with respect to inner shaft 24, which results in a fixed length of compartment 28. As illustrated, base member 200 is substantially symmetric about its longitudinal axis L. The components of base member 200 are preferably integrally formed, but in some embodiments one or more of the components may be separately formed and then coupled together.

Figure 5A:
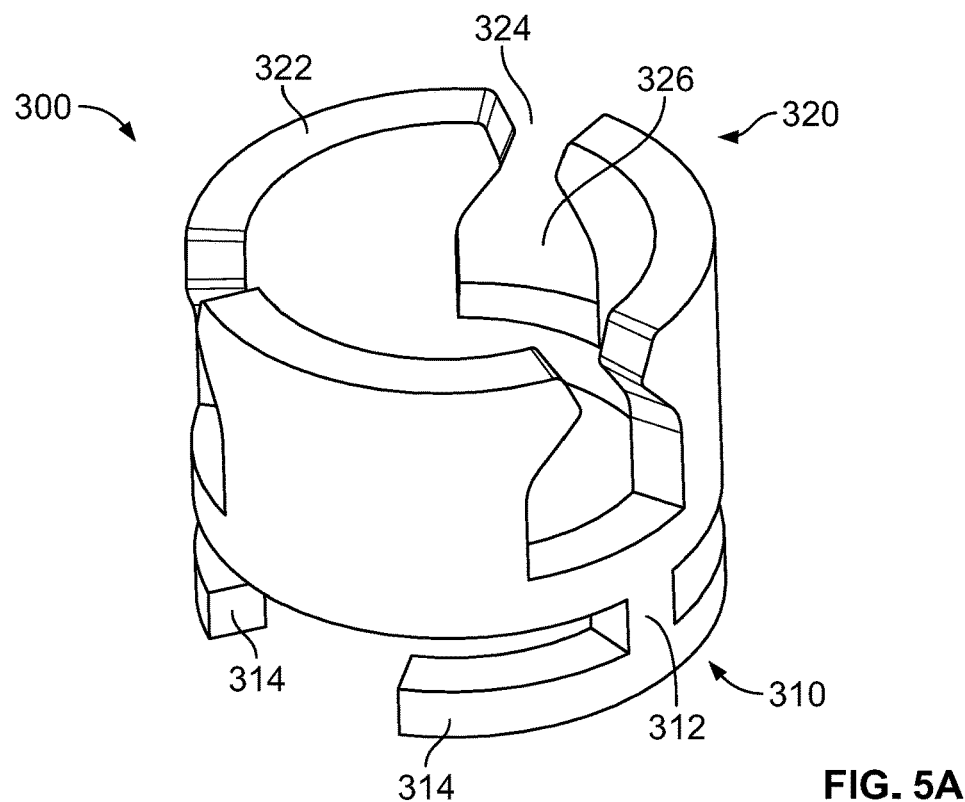
FIG. 5A is a perspective view of a first retaining member of the retaining assembly of FIG. 3.
Figure 5B:
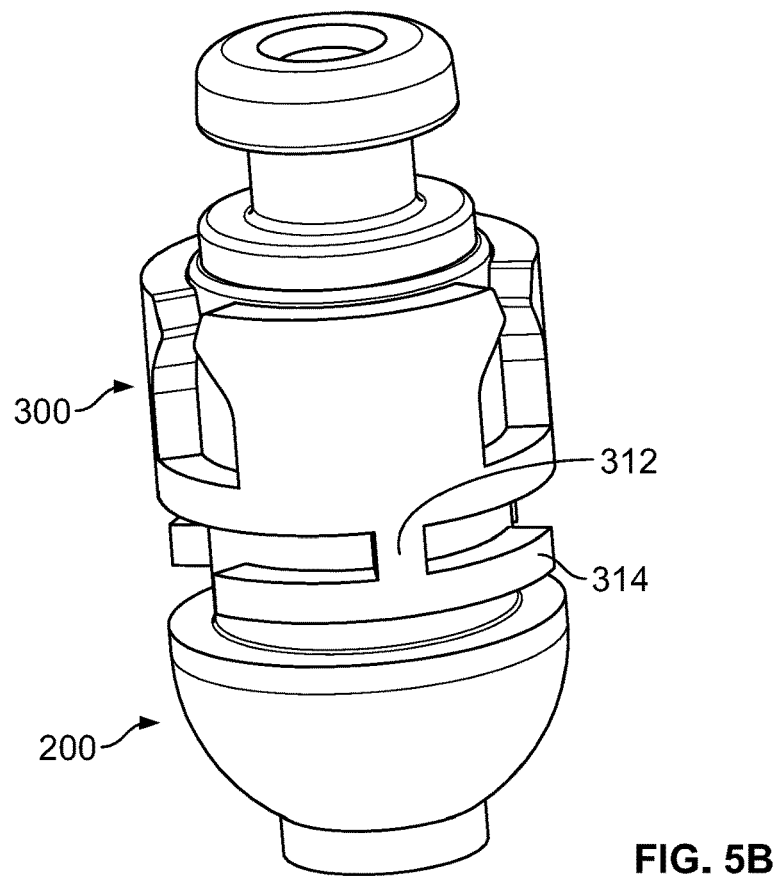
FIG. 5B is a perspective view of the first retaining member of FIG. 5A assembled to the base member of FIGS. 4A-B.

First retaining member 300 is illustrated isolated from the other components of retaining assembly 30 in FIG. 5A, while FIG. 5B illustrates first retaining member 300 assembled to base member 200, with all other components of retaining assembly 30 omitted for clarity of illustration. First retaining member 300 extends from a proximal end 310 to a distal end 320, and may be substantially cylindrical with a plurality of openings formed therein. The inside of first retaining member 300 may be substantially hollow and cylindrical, with a shape for receiving the intermediate portion 220 of base member 200 therein. Preferably, when assembled to base member 200, the first retaining member 300 is rotatable about the inner shaft 24 and about the longitudinal axis L of the base member. To allow for rotation, at least some clearance is preferably provided between the outer diameter of intermediate portion 220 and the inner diameter of first retaining member 300. The distal end 320 of first retaining member 300 may form a substantially circular rim 322, with a plurality of openings 324 interrupting the rim. In the illustrated embodiment, three openings 324 are positioned at substantially equal distances along the circumference of rim 322, although the number and position of the openings may be varied depending on the corresponding number and positions of the retainers of the prosthetic valve to be used with the delivery device. Each opening 324 may extend inward from rim 322 and lead to a retainer slot 326 sized and shaped to receive a retainer 118 of prosthetic valve 100. The width of openings 324 may be relatively small compared to the width of retainer slots 326. These relative dimensions correspond to portions of the retainers 118, so that when the retainers are positioned within corresponding slots 326, the larger width portions of the retainers are too large to pass through openings 324. In this configuration, when retainers 118 are positioned within slots 326, the prosthetic valve 100 may be completely or partially restricted from translational movement with respect to the first retaining member 300. It should be understood that the particular shape of retainer slots 326 may vary from that shown, and may be configured based on the size and shape of retainers 118.

Figure 5C:
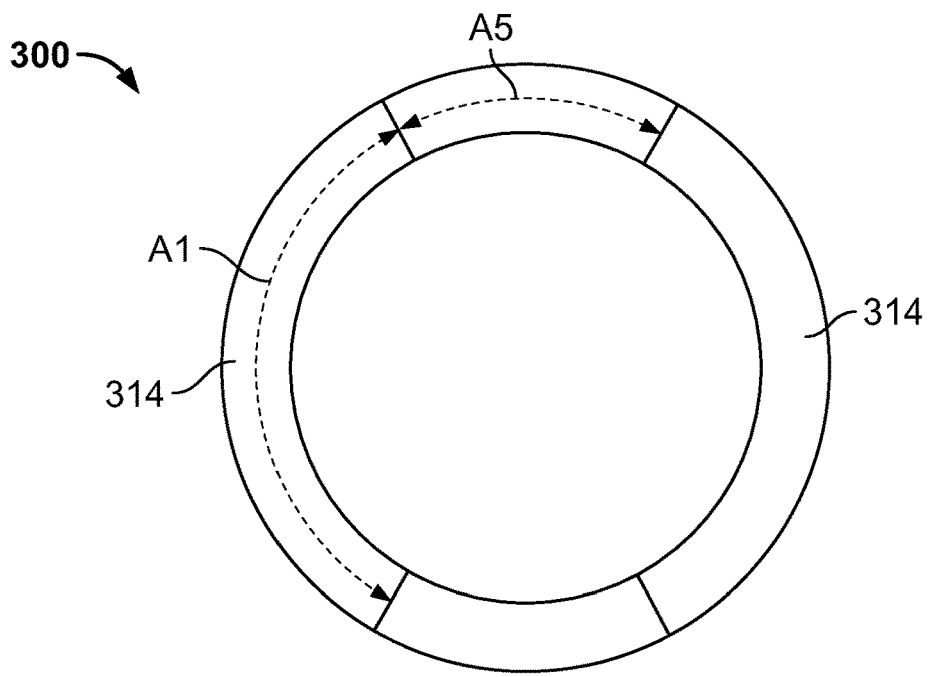
FIG. 5C is a bottom view of the first retaining member of FIG. 5A.
Figure 5D:
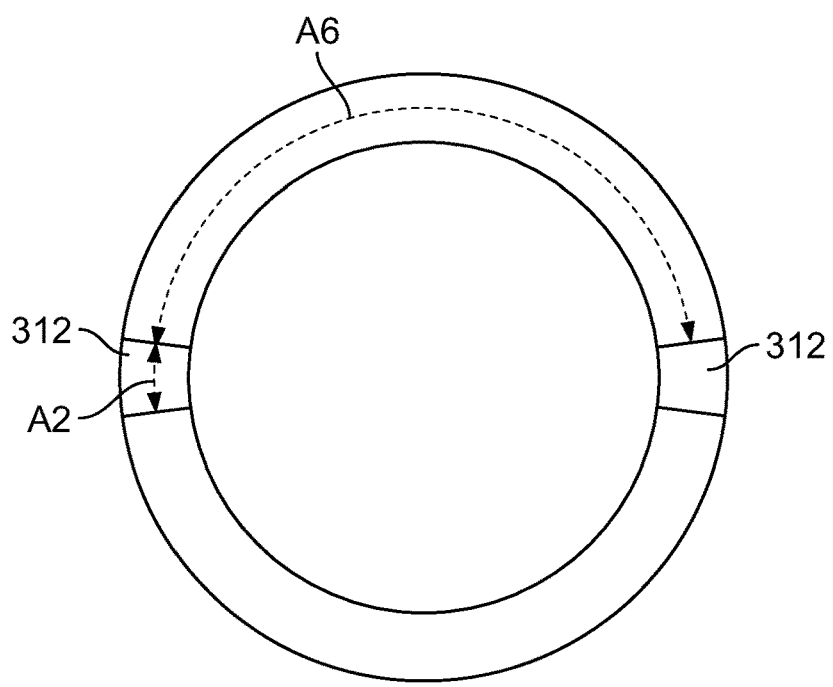
FIG. 5D is a bottom view of the first retaining member of FIG. 5A with arcuate flanges omitted from the drawing.

The proximal end 310 of first retaining member 300 may include two narrow extensions 312 each extending in the length direction of the first retaining member to a corresponding arcuate flange 314. FIG. 5C illustrates a bottom view of first retaining member 300, while FIG. 5D illustrates the same view but with the arcuate flanges 314 omitted. As shown in FIG. 5C, each arcuate flange 314 may have an arc length A1. As shown in FIG. 5D, each extension 312 may have an arc length A2. The arcuate space between adjacent ends of two flanges 314 may have an arcuate first slot length A5, while the arcuate space between the extensions 312 may have an arcuate second slot length A6. It should be understood that although two extensions 312 and two corresponding arcuate flanges 314 are shown, one of each item or more than two of each item may be provided depending on the configuration of the corresponding features of the second retaining member 400, described below. In the illustrated embodiment, the two extensions 312 are substantial mirror images of one another, as are the two arcuate flanges 314.

Figure 6A:
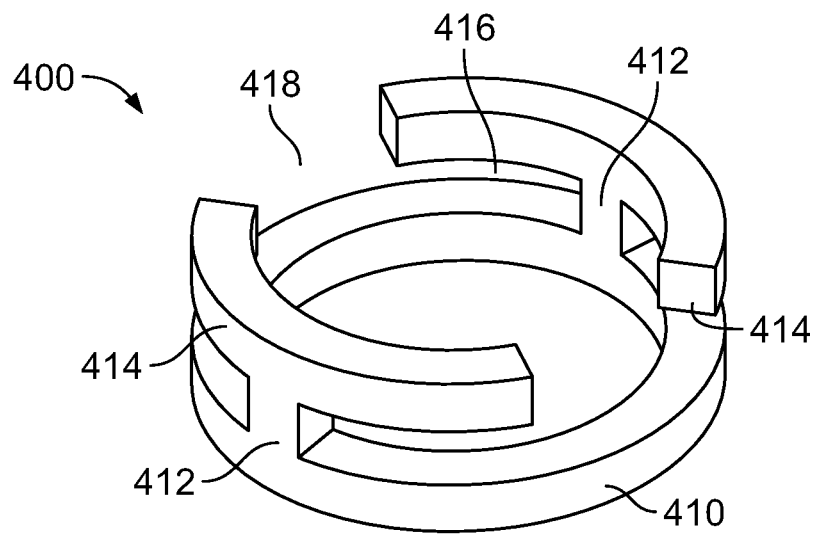
FIG. 6A is a perspective view of a second retaining member of the retaining assembly of FIG. 3.
Figure 6B:
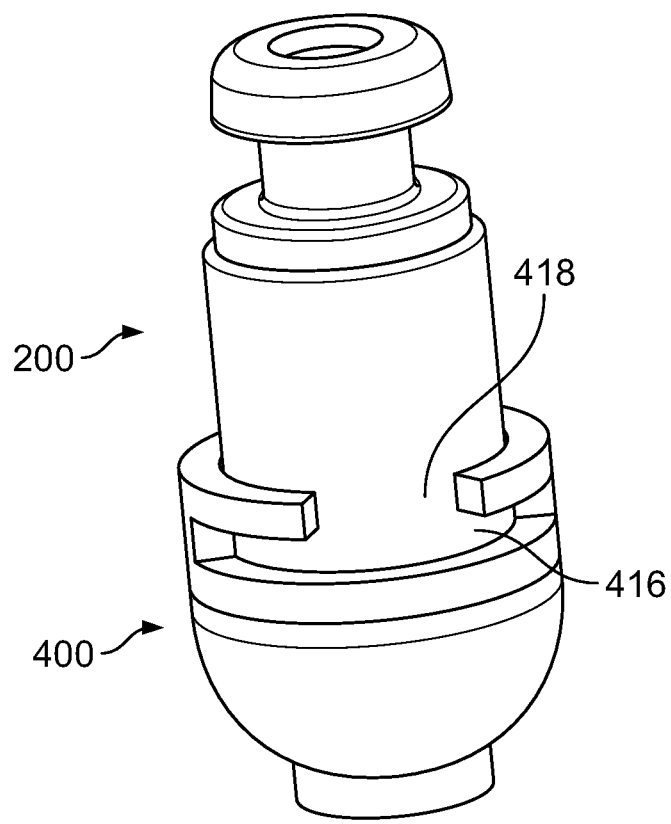
FIG. 6B is a perspective view of the second retaining member of FIG. 6A assembled to the base member of FIGS. 4A-B.

Second retaining member 400 is illustrated isolated from the other components retaining assembly 30 in FIG. 6A, while FIG. 6B illustrates second retaining member 400 assembled to base member 200, with all other components of retaining assembly 30 omitted for clarity of illustration. Second retaining member 400 includes a substantially cylindrical base 410 at a proximal end thereof. The inside of second retaining member 400 may be substantially hollow and cylindrical, with a shape for receiving the intermediate portion 220 of base member 200 therein. In particular, when the second retaining member 400 is assembled to base member 200, a proximal face of base 410 may contact shoulder 214 of support member 212. Preferably, second retaining member 400 is rotationally and translationally fixed with respect to the inner shaft 24 and the base member 200. This fixation may be achieved via welding (e.g. laser welding), by crimping second retaining member 400 to base member 200, using adhesives, or any other suitable method. Two narrow extensions 412 may each extend in the longitudinal direction of the second retaining member 400 from the base 410 to a corresponding arcuate flange 414. The spaces between the extensions 412 and base 410 may define a pair of arcuate slots 416. The spaces between confronting ends of the two arcuate flanges 414 in the circumferential direction may define openings 418 leading to arcuate slots 416. Although second retaining member 400 is illustrated with a pair of flanges 414 and slots 416, one of each item or more than two of each item may be provided, depending on the corresponding configuration of first retaining member 300.

Figure 6C:
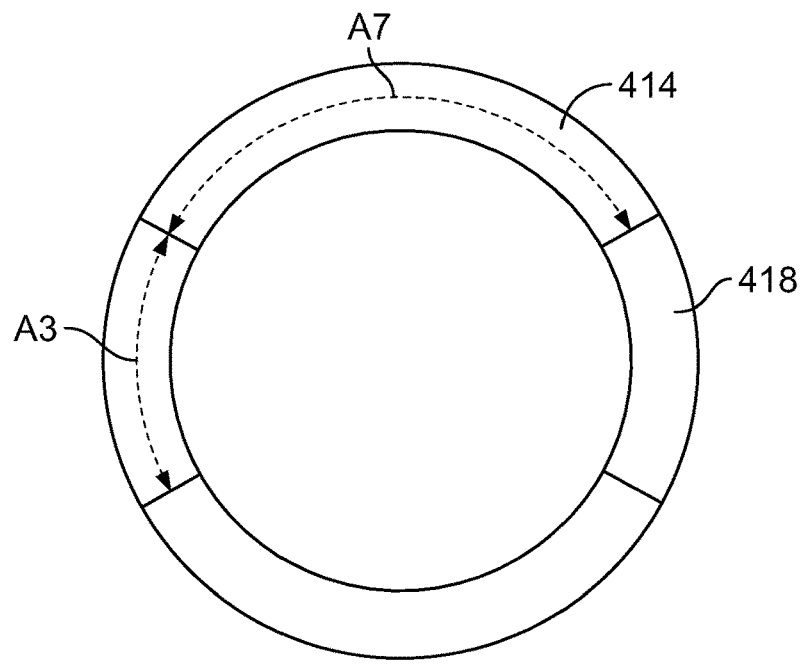
FIG. 6C is a top view of the second retaining member of FIG. 6A.
Figure 6D:
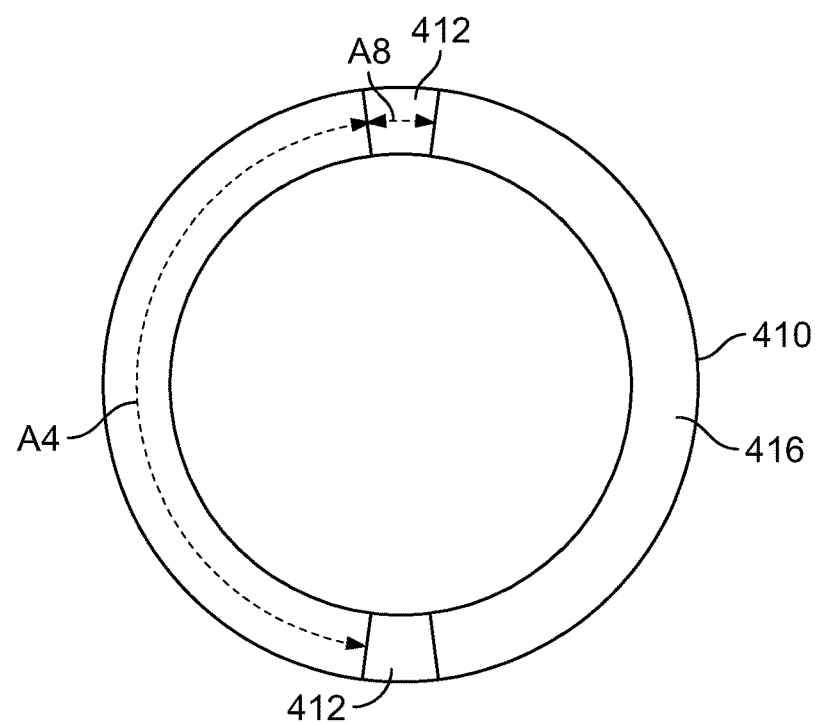
FIG. 6D is a top view of the second retaining member of FIG. 6A with arcuate flanges omitted from the drawing.

FIG. 6C illustrates a top view of second retaining member 400, while FIG. 6D illustrates the same view but with the arcuate flanges 414 omitted from the drawing for clarity of illustration. As shown in FIG. 6C, the spaces between the ends of confronting arcuate flanges 414 in the circumferential direction, otherwise referred to as openings 418, have an arc length A3. As shown in FIG. 6D, the spaces between extensions 412 in the circumferential direction, otherwise referred to as arcuate slots 412, have an arc length A4. Flanges 414 may have an arc length of A7, and extensions 412 may have an arc length of A8.

Figure 7A:
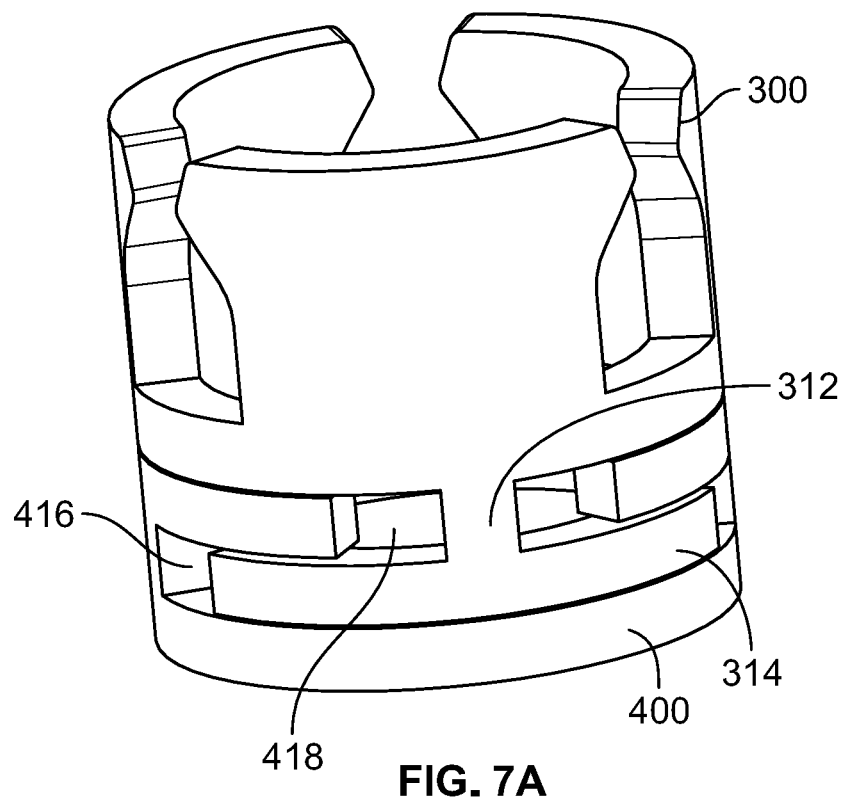
FIG. 7A is a perspective view of the first retaining member of FIG. 5A assembled to the second retaining member of FIG. 6A.
Figure 7B:
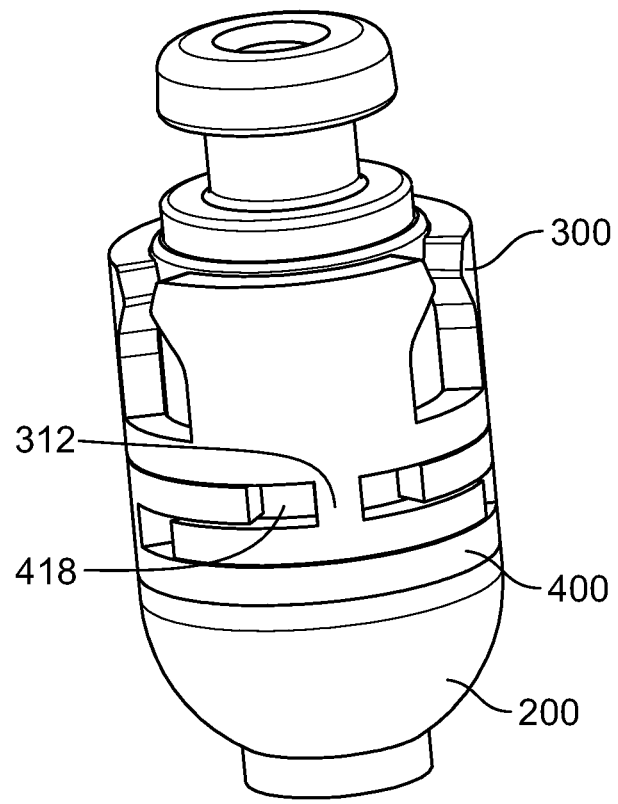
FIG. 7B is a perspective view of the first and second retaining members of FIG. 7A assembled to the base member of FIGS. 4A-B.

FIG. 7A shows the first retaining member 300 assembled to the second retaining member 400, while FIG. 7B shows the assembly of FIG. 7A assembled to the base member 200. Since first retaining member 300 is rotatable about the longitudinal axis L of the base member 200, and second retaining member 400 is rotationally fixed with respect to the longitudinal axis of the base member, the first retaining member is able to rotate with respect to the second retaining member. As can be seen in FIGS. 7A-B, first retaining member 300 and second retaining member 400 preferably have substantially the same radial thickness and circumferential profile. When assembled, extensions 312 of first retaining member 300 pass through corresponding openings 418 in the second retaining member 400, so that the arcuate flanges 314 of the first retaining member are disposed within corresponding slots 416 of the second retaining member. In order for extensions 312 to be able to pass through openings 418 and for first retaining member 300 to rotate relative to second retaining member 400, the arc length A2 of extensions 312 should be smaller than the arc length A3 of the openings 418. Similarly, the arc length A8 of extensions 412 should be smaller than the arc length A5 of the openings between the ends of flanges 314. Further, the arc length A1 of arcuate flanges 314 is greater than the arc length A3 of the openings 418. With this configuration the arcuate flanges 314 are too large to pass though the openings 418, so that translational movement between the first retaining member 300 and the second retaining member 400 is restricted in all rotational positions of the first retaining member. The arc length A1 of arcuate flanges 314 is smaller than the arc length A4 of slots 416, and the arc length A7 of flanges 414 is smaller than the arc length A6 of the slots between extensions 312. With this configuration, when first retaining member 300 is assembled to second retaining member 400 and base member 200, the first retaining member can be rotated about longitudinal axis L an extent based on the difference between arc length A1 and arc length A4, and/or the difference between arc length A7 and arc length A6. In other words, first retaining member 300 may be rotated until an end of an arcuate flange 314 contacts one of the extensions 412 of second retaining member 400 or until an end of an arcuate flange 414 contacts one of extensions 312 of first retaining member 300. In some embodiments, first retaining member 300 may be rotated more than 0 degrees but no more than 90 degrees about the longitudinal axis L. Although in some embodiments rotation of more than 90 degrees is possible, limiting the rotation to a maximum of 90 degrees (or less) may have certain benefits as described in greater detail below.

A method of using delivery device 10 to deploy prosthetic heart valve 100 into a patient is described below. In order to load delivery device 10 with prosthetic heart valve 100, a user attaches the retainers 118 of stent 102 into corresponding retainer slots 326 of first retaining member 300. The user then compresses or crimps the prosthetic valve 100 until it fits inside the outer sheath 22, which holds the valve in a compressed state. Referring to FIG. 2, when collapsed for delivery, the inflow end 130 of prosthetic valve 100 contacts the distal conical end 32 of delivery device 10, the outflow end 132 of the valve contacts the proximal conical end 31, and the outer sheath 22 is in distal extension so that it contacts the proximal end of distal tip 12 and covers compartment 28, holding the prosthetic valve securely in the collapsed condition.

With the prosthetic valve 100 crimped onto delivery device 10 within compartment 28, the user would advance the distal end of the delivery device to the site of implantation. The illustrated embodiment of delivery device 10 may be particularly suited for a transfemoral delivery route. As noted above, during advancement of the delivery device 10, an earlier positioned guidewire may be used, with the delivery device being advanced over the guidewire.

Once the compartment 28 of delivery device 10 is positioned at the site of implantation, for example within the native aortic valve annulus, a user may operate the proximal end of the delivery device (e.g., the handle attached to outer sheath 22 and inner shaft 24) to begin to deploy the prosthetic valve 100. It should be understood that, upon deployment of prosthetic valve 100, the stent 102 begins to expand radially outwardly so that the retainers 118 exit slots 326 by moving radially outward from first retaining member 300. However, prior to deployment when prosthetic heart valve 100 is maintained in a collapsed condition, outer sheath 22 overlies the prosthetic heart valve restricting the ability of the prosthetic heart valve to expand. With the illustrated embodiment, the outer sheath 22 may be moved proximally relative to inner shaft 24 to expose the inflow end 130 of prosthetic valve 100. As the prosthetic valve 100 is exposed, the radial constriction of the outer sheath 22 is removed and the prosthetic valve begins to re-expand. As long as retainers 118 of prosthetic valve 100 remain within retainer slots 326 and remain covered by outer sheath 22, the outflow end of prosthetic valve 100 remains coupled to delivery device 10, even if the inflow end has partially or fully expanded. The user may retract outer sheath 22 enough to allow much of the prosthetic valve 100, including valve assembly 140, to expand and to engage the native valve annulus. With the retainers 118 still coupling the prosthetic valve 100 to the retaining assembly 30, but with the valve assembly 140 mostly or entirely expanded in place, the user may test the prosthetic valve to determine whether the leaflets 108 are functioning correctly. If the operation and/or the position of prosthetic valve 100 is not satisfactory, the user may advance the outer sheath distally to re-collapse (or "resheath") the prosthetic valve. With the prosthetic valve 100 again collapsed in compartment 28, the user may attempt to reposition the valve.

Once the position and function of prosthetic valve 100 has been determined to be satisfactory, the user may attempt to fully deploy the prosthetic heart valve from delivery device 10. Usually, in order to deploy the prosthetic heart valve 100 completely, the outer sheath 22 would be retracted relative to inner shaft 24 until the retainer slots 326 are exposed, at which point the retainers 118 would expand radially outwardly and exit the retaining assembly 30. At that point, the prosthetic heart valve 100 would be fully implanted and no connections to the delivery device 10 would remain. However, some potential problems may arise prior to full deployment that the delivery device 10, and in particular the retaining assembly 30, is able to overcome.

One problem that may arise during deployment of the prosthetic heart valve 100 from compartment 28 may be caused by subjecting the prosthetic heart valve to twisting forces while it is in the compartment. For example, because the delivery device 10 may extend along a tortuous path in the vasculature, the prosthetic valve 100 may be subjected to a twisting or torqueing force along its length as the outer sheath 22 is curved or twisted. Other known delivery devices have failed to account for this potential problem, which could result in the valve unexpectedly or undesirably twisting upon deployment. This problem could also make it difficult for the retainers of the prosthetic heart valve to fully release from corresponding retainer slots if there are significant frictional forces acting between the retainers and the retainer slots. However, if prosthetic valve 100 is subjected to such twisting forces while it is coupled to retaining assembly 30, the first retaining member 300 would rotate about the longitudinal axis L of base member 200 to reach or move toward a state of equilibrium. For example, if the prosthetic valve 100 required rotation of 15 degrees about its longitudinal axis to reach a state of equilibrium, and the relative dimensions of first retaining member 300 and second retaining member 400 allowed for at least 15 degrees of rotation, the first retaining member would rotate up to 15 degrees while the prosthetic valve remained collapsed within compartment 28. As long as the twisting force acting in prosthetic valve 100 is greater than the friction between the collapsed valve and sheath 14 and the rotational friction between the first retaining member 300 and the base member 200, this rotation toward a state of equilibrium would occur naturally because the first retaining member is substantially free to rotate about the base member. As delivery device is advanced toward the implantation site, prosthetic valve 100 may rotate in both first and second directions depending on the twisting forces encountered. Thus, by the time the user attempts to deploy prosthetic valve 100, any twisting forces previously applied to the prosthetic valve will already have been compensated for by rotation of first retaining member 300.

In some embodiments, upon loading prosthetic valve 100 into compartment 28, the arcuate flanges 314 of first retaining member 300 may be positioned so that space is available between each end of each arcuate flange and an adjacent extension 412 of second retaining member 400. With this initial configuration, the prosthetic heart valve 100 is free to rotate in either direction about the longitudinal axis L of base member 200 initially. However, it should also be understood that with this initial configuration, the initial maximum extent of rotation of first retaining member 300 is about half of what the initial available maximum rotation would be if one end of each arcuate flange 314 was initially in contact with a corresponding extension 412. Although this latter configuration would double the initial maximum extent of rotation of first retaining member 300, only a single direction of rotation would initially be available. It should be understood that in some embodiments, upon loading prosthetic valve 100 into compartment 100, the arcuate flanges 314 of first retaining member 300 may be positioned so that space is only available between one end of each arcuate flange and an adjacent extension 412 of second retaining member 400.

In some embodiments, first retaining member 300 and second retaining member 400 may have dimensions relative to one another to allow for a large degree of rotation relative to one another. The advantage of a large degree of rotation of first retaining member 300 is that a large twisting force applied to the prosthetic valve 100 during delivery may be compensated for by the necessary amount of rotation of the first retaining member. However, providing only a limited degree of rotation of first retaining member 300 relative to second returning member 400 may also be desirable. For example, another problem that may arise during deployment of prosthetic valve 100 is that the retainers 118 may be pressed up against native anatomy as the outer sheath 22 is moved proximally relative to inner shaft 24 and clears the retainers. If this situation arises, the prosthetic valve 100 may not release from the retaining assembly 30 because, even though the outer sheath 22 is no longer keeping retainers 118 in retainer slots 326, the native anatomy may be doing just that. In order to rectify this situation, the user may attempt to rotate the prosthetic valve 100 about its longitudinal axis to move the affected retainer(s) 118 to a different position that is clear of the native anatomy. In order to rotate the prosthetic valve 100, the user would apply torque to retaining assembly 30, for example by rotating the handle or actuating a mechanism at the handle to cause such rotation. If there is space in the circumferential direction between the ends of the arcuate flanges 314 of the first retaining member and the corresponding extensions 412 of the second retaining member 400, the torque applied by the user might not actually rotate the prosthetic valve, but rather would rotate the second retaining member relative to the first retaining member. By limiting the difference between the arc length A1 of the arcuate flanges 314 and the arc length A4 of the slots 416, the user would be able to apply torque in the desired direction until an end of an arcuate flange of the first retaining member 300 contacts an extension 412 of the second retaining member 400. Once that contact occurs, applying additional torque in the same direction would result in the rotation of both the first retaining member 300 and the second retaining member 400, and thus rotation of prosthetic valve 100. The user could apply torque until the retaining members 118 cleared the obstruction, at which point the prosthetic valve 100 would fully disengage from the delivery device 10.

As should be understood from the two potential problems described above, there may be a tradeoff in benefits depending on the degree of rotation available for first retaining member 300 relative to second retaining member 400. It may be desirable to provide at least a minimum relative degree of rotation, for example up to about 90 degrees or up to about 180 degrees, to allow for compensation of the twisting forces encountered by prosthetic heart valve 100, but it may also be desirable to limit the relative degree of rotation so that a user can relatively easily intentionally rotate the prosthetic heart valve if deployment is obstructed.

Figures 8, 9:
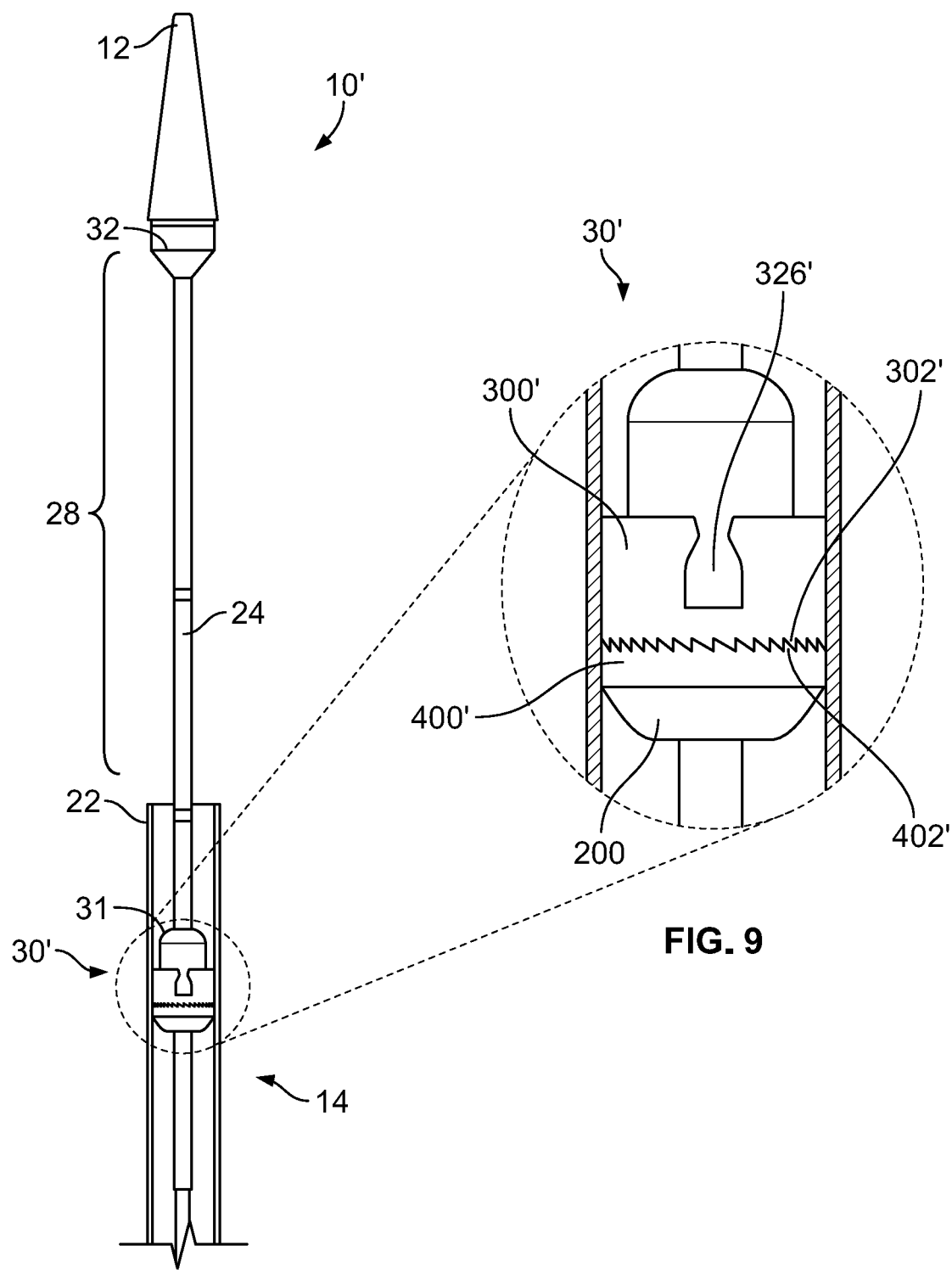
FIG. 8 is a side view of a distal portion of a transfemoral delivery device for a collapsible prosthetic heart valve according to another aspect of the disclosure.
FIG. 9 is an enlarged view of a retaining assembly of the delivery device of FIG. 8.

A delivery device 10' according to another aspect of the disclosure is shown in FIG. 8. Most components of delivery device 10' are identical to delivery device 10, and thus are not separately described. It should be understood that the components in FIG. 8 that have the same part numbers as those in FIG. 2 are substantially similar or identical. The main difference between delivery device 10' and delivery device 10 is the configuration of retaining assembly 30'. An enlarged view of retaining assembly 30' is illustrated in FIG. 9.

Retaining assembly 30' includes a base member that may be substantially similar or identical to base member 200 of retaining assembly 30, and is not described in additional detail. Retaining assembly 30' may also include a first retaining member 300' and a second retaining member 400'. First retaining member 300' and second retaining member 400' are shown in an exploded view in FIG. 10. Similar to second retaining member 400, second retaining member 400' may be positioned around base member 200 and in contact with a shoulder of base member 200. Second retaining member 400' may be translationally and rotationally fixed with respect to base member 200 and the longitudinal axis of inner shaft 24. Such fixation may be obtained by crimping second retaining member 400' to base member 200, by adhesives, or by any other suitable method. First retaining member 300' may include a plurality of retainer slots 326' having a configuration that is substantially the same as or identical to the retainer slots 326 of first retaining member 300.

Figure 10:
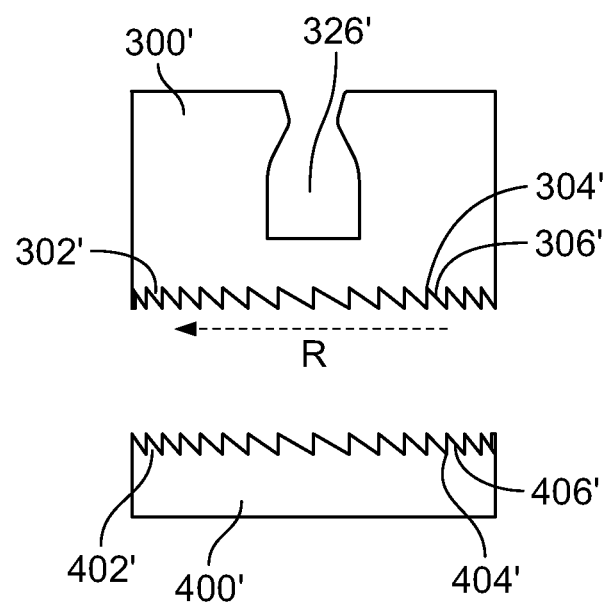
FIG. 10 is an exploded view of a first retaining member and second retaining member of the retaining assembly of FIG. 9.

Whereas first retaining member 300 is rotatable in either direction about inner shaft 24 with a limited range of rotation, first retaining member 300' is rotatable about the inner shaft in only a single direction, but the range of rotation is unlimited. In the illustrated embodiment, this function is achieved via a ratchet-type mechanism. Referring to FIG. 10, at the end confronting second retaining member 400' first retaining member 300' may have a substantially cylindrical rim with a plurality of first teeth 302' extending along the circumference of the rim. Similarly, at the end confronting first retaining member 300', second retaining member 400' may have a substantially cylindrical rim with a plurality of second teeth 402' extending along the circumference of the rim. Each tooth 302' may include a first longitudinal portion 304' extending in a direction substantially parallel to the inner shaft 24, and a second portion 306' extending at an angle to the inner shaft between two adjacent longitudinal portions. Each tooth 402' may have a similar configuration with longitudinal portions 404' and angled portions 406'. With this configuration, first retaining member 300' is capable of ratchet-like rotation in the direction R with respect to second retaining member 400'. In other words, viewing delivery device 10' on end from the distal tip 12, first retaining member 300' is capable of clockwise rotation about inner shaft 24, but is substantially incapable of counterclockwise rotation about the inner shaft.

In some embodiments, delivery device 10' allows for complete or nearly complete compensation for twisting forces exerted on prosthetic heart valve 100 while it is coupled to retainer slots 326' in the collapsed condition, but only if those twisting forces are exerted in the direction in which first retaining member 300' is free to rotate. The material properties and particular shape of teeth 302' and 402' may dictate the amount of friction between corresponding teeth of the first retaining member 300' and the second retaining member 400'. By providing teeth 302' and 402' with respective longitudinal sections 304' and 404' that have a small length, for example between about 0.005 and about 0.02 inches, the first retaining member 300' may be substantially free to rotate in the direction R, but substantially incapable of rotating in the opposite direction because the angle of angled sections 306', 406' to be overcome is shallow, resulting in a relatively small contact friction between the angled sections as they move past one another. In some embodiments, the teeth 302' and 402' may be formed of a compressible material, enabling the teeth to deform slightly to facilitate rotation of the first retaining member 300' in the direction R. On the other hand, increasing the length of longitudinal sections 304' and 404' will increase the angle of angled sections 306', 406', making it more difficult to rotate the first retaining member 300' relative to the second retaining member 400'.

As noted above, first retaining member 300' may be substantially free to rotate through an unlimited range in the direction R with respect to second retaining member 400' to alleviate twisting forces exerted on the prosthetic heart valve 100 in the same direction. However, the engagement between teeth 302' and 402' prevents first retaining member 300' from rotating with respect to second retaining member 400' in the direction opposite the direction R. Thus, if a user encounters a situation in which the prosthetic heart valve 100 needs to be rotated, for example to clear native anatomy obstructing retainers 118 from being released from retainer slots 326', the user may intentionally rotate the second retaining member 400' in the direction R about a longitudinal axis of the retaining assembly 30', for example, by rotating inner shaft 24 in that direction. Since second retaining member 400' is rotationally fixed through base member 200 to inner shaft 24, torque applied to the inner shaft is transmitted to the second retaining member. As second retaining member 400' is rotated in direction R, the engagement of teeth 402' with teeth 302' will cause first retaining member 300' to also rotate in the same direction. However, the user may not be able to significantly rotate the retaining assembly 30' in the direction opposite the direction R by applying torque in that direction to second retaining member 400', as the orientation of teeth 302' and 402' enable the first retaining member 300' and the second retaining member 400' to rotate relative to one another in that direction.

Although the retaining assemblies 30 and 30' are illustrated on the proximal end of compartment 28, it should be understood that in some embodiments the retaining assemblies may be positioned on the distal end of the compartment with the first retaining members 300 and 300' being positioned proximal to the corresponding second retaining members 400 and 400'. The particular position of the retaining assembly 30 or 30' may depend on the type of valve being delivered, which end of the valve is desired to be released last from the delivery device, and the delivery route. For example, it is generally preferable that a valve assembly within the stent be capable of completely or substantially completely expanding prior to the stent disconnecting from the retaining assembly so that proper operation of the valve assembly may be confirmed prior to fully releasing the prosthetic heart valve from the delivery device.

According to a first aspect of the disclosure, a delivery device is for an implantable medical device having at least one retainer thereon, the delivery device comprising:

an inner shaft extending in a longitudinal direction;

an outer sheath adapted to surround at least a portion of the inner shaft, the outer sheath being slideable relative to the inner shaft in the longitudinal direction;

a compartment defined between the inner shaft and the outer sheath and adapted to receive the medical device in an assembled condition;

a retaining assembly positioned at one end of the compartment, the retaining assembly including a first member rotatable with respect to the inner shaft, and a second member rotationally fixed with respect to the inner shaft; and at least one retainer slot in the first member adapted to receive the retainer of the medical device in the assembled condition, wherein engagement between the first member and the second member limits rotation of the first member; and/or the second member includes an arcuate slot and the first member includes an arcuate flange received within the arcuate slot; and/or the arcuate flange includes first and second terminal ends and the second member includes at least one extension at least partially defining the arcuate slot; and/or the at least one extension includes a first extension and a second extension, the first member being configured to rotate between a first position in which the first terminal end contacts the first extension and a second position in which the second terminal end contacts the second extension, a maximum range of rotation of the first member being defined by the first position and the second position; and/or the maximum range of rotation is between 0 degrees and 90 degrees; and/or the first member includes a first rim having a plurality of first teeth extending along a circumference thereof, and the second member includes a second rim having a plurality of second teeth extending along a circumference thereof; and/or the plurality of first teeth are in ratcheting engagement with the plurality of second teeth so that the first member is capable of rotation about the inner shaft in a first direction but substantially incapable of rotating about the inner shaft in a second direction opposite the first direction; and/or the first member is capable of unlimited rotation about the inner shaft in the first direction; and/or the delivery device and the medical device comprise a system; and/or the medical device is a collapsible prosthetic heart valve including a valve assembly mounted within a stent, the stent including a plurality of retainers and the first member including a plurality of retainer slots, each of the retainers being receivable within a corresponding one of the retainer slots; and/or the prosthetic heart valve extends from an inflow end to an outflow end, the plurality of retainers being positioned on the outflow end of the prosthetic valve.

According to a second aspect of the disclosure, a method of delivering a collapsible prosthetic valve to a patient comprises:

providing the collapsible prosthetic valve having a collapsible valve assembly mounted within a collapsible stent, the stent having a plurality of retainers extending therefrom;

providing a delivery device including:
an inner shaft extending in a longitudinal direction;
an outer sheath adapted to surround at least a portion of the inner shaft;
a compartment defined between the inner shaft and the outer sheath; and a retaining assembly positioned at one end of the compartment, the retaining assembly including a first member rotatable with respect to the inner shaft and a second member rotationally fixed with respect to the inner shaft;

loading the collapsible prosthetic valve into the compartment in a collapsed condition so that the retainers are received within corresponding retainer slots of the first member;

advancing the compartment to a site of implantation in the patient;

rotating the first member relative to the second member during the advancing step, wherein engagement between the first member and the second member limits rotation of the first member; and exposing the compartment by sliding the outer sheath relative to the inner shaft so that the collapsible prosthetic valve at least partially expands; and/or the rotating step includes rotating an arcuate flange of the first member within an arcuate slot of the second member; and/or the arcuate flange includes first and second terminal ends and the second member includes at least one extension at least partially defining the arcuate slot; and/or the at least one extension includes a first extension and a second extension, and the rotating step includes rotating the first member between a first position in which the first terminal end contacts the first extension and a second position in which the second terminal end contacts the second extension, the first member having a maximum range of rotation defined by the first position and the second position; and/or the loading step includes loading the collapsible prosthetic valve into the compartment so that the first terminal end is a spaced distance from the first extension and the second terminal end is a spaced distance from the second extension; and/or during the advancing step, a plurality of first teeth extending along a circumference of a first rim of the first member are engaged with a plurality of second teeth extending from a circumference of a second rim of the second member; and/or during the advancing step, the plurality of first teeth are in ratcheting engagement with the plurality of second teeth so that the first member rotatable with respect to the inner shaft in a first direction but substantially incapable of rotating with respect to the inner shaft in a second direction opposite the first direction; and/or allowing forces exerted upon the prosthetic valve to cause the first member to rotate with respect to the inner shaft and relative to the second member while the compartment is within the patient; and/or manually rotating the delivery device to cause both the first member and the second member to rotate about a longitudinal axis extending from a proximal end of the retaining assembly to a distal end of the retaining assembly while the compartment is within the patient.

Although the invention herein has been described with reference to particular embodiments, it is to be understood that these embodiments are merely illustrative of the principles and applications of the present invention. It is therefore to be understood that numerous modifications may be made to the illustrative embodiments, including features of one embodiment being combined with features of another embodiment, and that other arrangements may be devised without departing from the spirit and scope of the present invention as defined by the appended claims.

The invention claimed is:

1. A delivery device for an implantable medical device having at least one retainer thereon, the delivery device comprising:
 an inner shaft extending in a longitudinal direction;
 an outer sheath adapted to surround at least a portion of the inner shaft, the outer sheath being slideable relative to the inner shaft in the longitudinal direction;
 a compartment defined between the inner shaft and the outer sheath and adapted to receive the medical device in an assembled condition;
 a retaining assembly positioned at one end of the compartment, the retaining assembly including a first member rotatable with respect to the inner shaft, and a second member rotationally fixed with respect to the inner shaft; and
 at least one retainer slot in the first member adapted to receive the retainer of the medical device in the assembled condition,
 wherein engagement between the first member and the second member limits rotation of the first member.

2. The delivery device of claim 1, wherein the second member includes an arcuate slot and the first member includes an arcuate flange received within the arcuate slot.

3. The delivery device of claim 2, wherein the arcuate flange includes first and second terminal ends and the second member includes at least one extension at least partially defining the arcuate slot.

4. The delivery device of claim 3, wherein the at least one extension includes a first extension and a second extension, the first member being configured to rotate between a first position in which the first terminal end contacts the first extension and a second position in which the second terminal end contacts the second extension, a maximum range of rotation of the first member being defined by the first position and the second position.

5. The delivery device of claim 4, wherein the maximum range of rotation is between 0 degrees and 90 degrees.

6. The delivery device of claim 1, wherein the first member includes a first rim having a plurality of first teeth extending along a circumference thereof, and the second member includes a second rim having a plurality of second teeth extending along a circumference thereof.

7. The delivery device of claim 6, wherein the plurality of first teeth are in ratcheting engagement with the plurality of second teeth so that the first member is capable of rotation about the inner shaft in a first direction but substantially incapable of rotating about the inner shaft in a second direction opposite the first direction.

8. The delivery device of claim 7, wherein the first member is capable of unlimited rotation about the inner shaft in the first direction.

9. A system for delivering a medical device to a patient, the system comprising:
 the delivery device of claim 1; and
 the medical device.

10. The system of claim 9, wherein the medical device is a collapsible prosthetic heart valve including a valve assembly mounted within a stent, the stent including a plurality of retainers and the first member including a plurality of retainer slots, each of the retainers being receivable within a corresponding one of the retainer slots.

11. The system of claim 10, wherein the prosthetic heart valve extends from an inflow end to an outflow end, the plurality of retainers being positioned on the outflow end of the prosthetic valve.

12. A method of delivering a collapsible prosthetic valve to a patient comprising:
 providing the collapsible prosthetic valve having a collapsible valve assembly mounted within a collapsible stent, the stent having a plurality of retainers extending therefrom;
 providing a delivery device including:
  an inner shaft extending in a longitudinal direction;
  an outer sheath adapted to surround at least a portion of the inner shaft;
  a compartment defined between the inner shaft and the outer sheath; and
  a retaining assembly positioned at one end of the compartment, the retaining assembly including a first member rotatable with respect to the inner shaft and a second member rotationally fixed with respect to the inner shaft;
 loading the collapsible prosthetic valve into the compartment in a collapsed condition so that the retainers are received within corresponding retainer slots of the first member;
 advancing the compartment to a site of implantation in the patient;
 rotating the first member relative to the second member during the advancing step, wherein engagement between the first member and the second member limits rotation of the first member; and
 exposing the compartment by sliding the outer sheath relative to the inner shaft so that the collapsible prosthetic valve at least partially expands.

13. The method of claim 12, wherein the rotating step includes rotating an arcuate flange of the first member within an arcuate slot of the second member.

14. The method of claim 13, wherein the arcuate flange includes first and second terminal ends and the second member includes at least one extension at least partially defining the arcuate slot.

15. The method of claim 14, wherein the at least one extension includes a first extension and a second extension, and the rotating step includes rotating the first member between a first position in which the first terminal end contacts the first extension and a second position in which the second terminal end contacts the second extension, the first member having a maximum range of rotation defined by the first position and the second position.

16. The method of claim 15, wherein the loading step includes loading the collapsible prosthetic valve into the compartment so that the first terminal end is a spaced distance from the first extension and the second terminal end is a spaced distance from the second extension.

17. The method of claim 12, wherein during the advancing step, a plurality of first teeth extending along a circumference of a first rim of the first member are engaged with a plurality of second teeth extending from a circumference of a second rim of the second member.

18. The method of claim 17, wherein during the advancing step, the plurality of first teeth are in ratcheting engagement with the plurality of second teeth so that the first member rotatable with respect to the inner shaft in a first direction but substantially incapable of rotating with respect to the inner shaft in a second direction opposite the first direction.

19. The method of claim 12, further comprising allowing forces exerted upon the prosthetic valve to cause the first member to rotate with respect to the inner shaft and relative to the second member while the compartment is within the patient.

20. The method of claim 12, further comprising manually rotating the delivery device to cause both the first member and the second member to rotate about a longitudinal axis extending from a proximal end of the retaining assembly to a distal end of the retaining assembly while the compartment is within the patient.

\* \* \* \* \*